US010383572B2

(12) United States Patent
Knickerbocker et al.

(10) Patent No.: US 10,383,572 B2
(45) Date of Patent: Aug. 20, 2019

(54) VIA AND TRENCH FILLING USING INJECTION MOLDED SOLDERING

(71) Applicant: International Business Machines Corporation, Armonk, NY (US)

(72) Inventors: John U. Knickerbocker, Monroe, NY (US); Shriya Kumar, New York, NY (US); Jae-Woong Nah, Closter, NJ (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/610,885

(22) Filed: Jun. 1, 2017

(65) Prior Publication Data

US 2018/0005932 A1 Jan. 4, 2018

Related U.S. Application Data

(60) Division of application No. 15/214,914, filed on Jul. 20, 2016, now Pat. No. 9,761,516, which is a
(Continued)

(51) Int. Cl.
*H05K 3/40* (2006.01)
*A61B 5/00* (2006.01)
(Continued)

(52) U.S. Cl.
CPC ............... *A61B 5/68* (2013.01); *A61M 5/00* (2013.01); *B23K 3/0638* (2013.01); *H01L 21/486* (2013.01); *H01L 21/76816* (2013.01); *H01L 21/76852* (2013.01); *H01L 21/76883* (2013.01); *H01L 21/76898* (2013.01);
(Continued)

(58) Field of Classification Search
CPC ............ H01L 23/49827; H01L 21/486; H01L 23/49838; H01L 21/76877; H01L 23/481; H01L 23/5226; H01L 23/5384; H05K 1/0306
See application file for complete search history.

(56) References Cited

U.S. PATENT DOCUMENTS 6,461,136 B1 10/2002 Gruber et al.
7,361,593 B2 4/2008 Freeman et al.
(Continued)

OTHER PUBLICATIONS

Paul Dempsey, "TSMC Hints at Glass Interposer for Mobile SoCs," http://www.techdesignforums.com/blog/2013/12/16/tsmc-glass-interposer-mobile-socs/, Dec. 16, 2013, 4 pages.
(Continued)

*Primary Examiner* — Bitew A Dinke
(74) *Attorney, Agent, or Firm* — L. Jeffrey Kelly; Ryan, Mason & Lewis, LLP

(57) ABSTRACT

A method includes forming one or more vias in a substrate, forming a first photoresist layer on a top surface of the substrate and a second photoresist layer on a bottom surface of the substrate, patterning the first photoresist layer and the second photoresist layer to remove at least a first portion of the first photoresist layer and at least a second portion of the second photoresist layer, filling the one or more vias, the first portion and the second portion with solder material using injection molded soldering, and removing remaining portions of the first photoresist layer and the second photoresist layer.

20 Claims, 11 Drawing Sheets

Related U.S. Application Data continuation of application No. 15/196,558, filed on Jun. 29, 2016, now Pat. No. 10,130,302.

(51) Int. Cl.

| | | |
|---|---|---|
| *H01L 21/768* | (2006.01) | |
| *H01L 23/498* | (2006.01) | |
| *H01L 23/532* | (2006.01) | |
| *H01L 21/48* | (2006.01) | |
| *H05K 1/03* | (2006.01) | |
| *H01L 23/00* | (2006.01) | |
| *A61M 5/00* | (2006.01) | |
| *B23K 3/06* | (2006.01) | |
| *H01L 23/66* | (2006.01) | |
| *H01L 23/13* | (2006.01) | |
| *H01L 23/15* | (2006.01) | |
| *B23K 101/36* | (2006.01) | |
| *H01L 23/538* | (2006.01) | |
| *H01L 23/14* | (2006.01) | |

(52) U.S. Cl.
CPC ........ *H01L 23/13* (2013.01); *H01L 23/49811* (2013.01); *H01L 23/49827* (2013.01); *H01L 23/49838* (2013.01); *H01L 23/53228* (2013.01); *H01L 23/53238* (2013.01); *H01L 23/53242* (2013.01); *H01L 23/53252* (2013.01); *H01L 23/53266* (2013.01); *H01L 23/66* (2013.01); *H01L 24/19* (2013.01); *H01L 24/20* (2013.01); *H01L 24/27* (2013.01); *H01L 24/32* (2013.01); *H01L 24/64* (2013.01); *H01L 24/69* (2013.01); *H01L 24/83* (2013.01); *H01L 24/89* (2013.01); *H05K 1/0306* (2013.01); *H05K 3/4038* (2013.01); *A61B 2562/12* (2013.01); *A61M 2207/00* (2013.01); *B23K 2101/36* (2018.08); *H01L 23/147* (2013.01); *H01L 23/15* (2013.01); *H01L 23/5389* (2013.01); *H01L 23/53233* (2013.01); *H01L 2223/6677* (2013.01); *H01L 2224/27312* (2013.01); *H01L 2224/325* (2013.01); *H01L 2224/32111* (2013.01); *H01L 2224/32235* (2013.01); *H01L 2224/64* (2013.01); *H01L 2224/69* (2013.01); *H01L 2224/83801* (2013.01); *H01L 2224/89* (2013.01); *H01L 2224/96* (2013.01); *H01L 2924/014* (2013.01); *H01L 2924/1434* (2013.01); *H01L 2924/15332* (2013.01); *H05K 2201/0305* (2013.01)

(56) References Cited

U.S. PATENT DOCUMENTS

| | | | |
|---|---|---|---|
| 7,687,916 B2 | 3/2010 | Lake | |
| 7,928,585 B2 | 4/2011 | Buchwalter et al. | |
| 8,117,982 B2 | 2/2012 | Gruber et al. | |
| 8,424,388 B2 | 4/2013 | Mattes et al. | |
| 8,552,556 B1* | 10/2013 | Kim | H01L 23/16 257/685 |
| 8,691,607 B2 | 4/2014 | Ararao | |
| 8,872,312 B2 | 10/2014 | Wang et al. | |
| 9,224,666 B2* | 12/2015 | Ziegler | H01L 24/27 |
| 2001/0027842 A1 | 10/2001 | Curcio et al. | |
| 2002/0114133 A1 | 8/2002 | Ho et al. | |
| 2002/0182508 A1 | 12/2002 | Nimon et al. | |
| 2003/0043316 A1* | 3/2003 | Matsumoto | G02F 1/1347 349/84 |
| 2007/0013051 A1 | 1/2007 | Heyan et al. | |
| 2007/0013062 A1 | 1/2007 | Kobayashi et al. | |
| 2007/0026567 A1 | 2/2007 | Beer et al. | |
| 2007/0045780 A1 | 3/2007 | Akram et al. | |
| 2007/0080864 A1 | 4/2007 | Channabasappa | |
| 2008/0029850 A1 | 2/2008 | Hedler et al. | |
| 2008/0102096 A1 | 5/2008 | Molin et al. | |
| 2008/0164573 A1 | 7/2008 | Basker et al. | |
| 2008/0272466 A1 | 11/2008 | Lake | |
| 2009/0015485 A1 | 1/2009 | Floyd et al. | |
| 2009/0032946 A1* | 2/2009 | Park | H01L 23/49816 257/738 |
| 2009/0065555 A1 | 3/2009 | Buchwalter et al. | |
| 2009/0091024 A1 | 4/2009 | Zeng et al. | |
| 2009/0121323 A1 | 5/2009 | Kwon et al. | |
| 2009/0267194 A1 | 10/2009 | Chen | |
| 2009/0267221 A1 | 10/2009 | Fujii | |
| 2009/0294974 A1 | 12/2009 | Leung et al. | |
| 2009/0294983 A1 | 12/2009 | Cobbley et al. | |
| 2010/0149046 A1 | 1/2010 | Huang et al. | |
| 2010/0109142 A1 | 5/2010 | Toh et al. | |
| 2011/0032685 A1 | 2/2011 | Akiba et al. | |
| 2011/0163457 A1 | 7/2011 | Mohan et al. | |
| 2011/0233762 A1 | 9/2011 | Gruber et al. | |
| 2011/0237030 A1* | 9/2011 | Gruber | H01L 21/486 438/111 |
| 2011/0248180 A1 | 10/2011 | Alexopoulos et al. | |
| 2012/0010698 A1 | 1/2012 | Hwang et al. | |
| 2012/0142144 A1 | 6/2012 | Taheri | |
| 2012/0161305 A1 | 6/2012 | Ruben et al. | |
| 2012/0161326 A1 | 6/2012 | Choi et al. | |
| 2012/0205694 A1* | 8/2012 | Chern | H01L 24/97 257/98 |
| 2012/0234902 A1 | 9/2012 | Chey et al. | |
| 2012/0286428 A1 | 11/2012 | Sakuma | |
| 2012/0288995 A1 | 11/2012 | El-Ghoroury et al. | |
| 2013/0009320 A1 | 1/2013 | Yoo et al. | |
| 2013/0026645 A1 | 1/2013 | Mohammed et al. | |
| 2013/0082364 A1 | 4/2013 | Wang et al. | |
| 2013/0093091 A1 | 4/2013 | Ma et al. | |
| 2013/0098669 A1 | 4/2013 | Yoshimura | |
| 2013/0189935 A1 | 7/2013 | Nair et al. | |
| 2013/0200517 A1* | 8/2013 | Wu | H01L 23/3121 257/741 |
| 2013/0200524 A1 | 8/2013 | Han et al. | |
| 2013/0313718 A1* | 11/2013 | Varghese | H01L 22/12 257/774 |
| 2013/0330878 A1* | 12/2013 | Ararao | H01L 21/56 438/107 |
| 2014/0003009 A1* | 1/2014 | Ma | H01L 23/49816 361/757 |
| 2014/0110841 A1 | 4/2014 | Beer et al. | |
| 2014/0168014 A1 | 6/2014 | Chih et al. | |
| 2014/0210082 A1 | 7/2014 | Kubota et al. | |
| 2015/0070228 A1 | 3/2015 | Gu et al. | |
| 2015/0243584 A1* | 8/2015 | Lu | H01L 21/76898 257/772 |
| 2015/0325908 A1 | 11/2015 | Reuter | |
| 2016/0035666 A1 | 2/2016 | Huang et al. | |
| 2016/0163668 A1 | 6/2016 | Hine et al. | |
| 2016/0233178 A1 | 8/2016 | Lamy et al. | |
| 2016/0240492 A1 | 8/2016 | Wolter et al. | |
| 2016/0307623 A1 | 10/2016 | Fang et al. | |
| 2016/0307823 A1* | 10/2016 | Fang | H01L 23/481 |
| 2017/0010301 A1 | 1/2017 | Bleselt et al. | |
| 2017/0018492 A1* | 1/2017 | Imayoshi | H01L 23/49894 |
| 2017/0033062 A1 | 2/2017 | Liu et al. | |

OTHER PUBLICATIONS

K. Cheolbok et al., "Through-Glass Interposer integrated High Quality RF Components," IEEE 64th Electronic Components and Technology Conference (ECTC), May 27-30, 2014, pp. 1103-1109.
Y. Orii et al., "Introduction of IMS Technology for Advanced Solder Bumping on Wafers/Laminates," SEMICON, Sep. 2014, 22 pages.
List of IBM Patents or Patent Applications Treated as Related.

* cited by examiner

100

200

210

300

310

400

500

600

700

800

900

1000

1850

1900

2000

2300

2400

2500

VIA AND TRENCH FILLING USING INJECTION MOLDED SOLDERING

CROSS-REFERENCE TO RELATED APPLICATION

This application is a divisional of U.S. patent application Ser. No. 15/214,914, filed Jul. 20, 2016, which is a continuation of U.S. patent application Ser. No. 15/196,558, filed Jun. 29, 2016, the disclosures of which are incorporated by reference herein. This application is also related to U.S. patent application Ser. Nos. 15/214,935 and 15/214,942, each of which was filed Jul. 20, 2016 and is a continuation of U.S. patent application Ser. No. 15/196,558.

BACKGROUND

The present application relates to trenches and vias, and more specifically, to techniques for filling trenches and/or vias. Trenches and vias are often used to interconnect components in electronic structures, such as integrated circuits, semiconductor structures, etc. Trenches and vias may also be used to facilitate bonding different layers to one another in electronic and other structures.

SUMMARY

Embodiments of the invention provide techniques for via and trench filling using injection molded soldering (IMS).

For example, in one embodiment a method comprises forming one or more vias in a substrate, forming a first photoresist layer on a top surface of the substrate and a second photoresist layer on a bottom surface of the substrate, patterning the first photoresist layer and the second photoresist layer to remove at least a first portion of the first photoresist layer and at least a second portion of the second photoresist layer, filling the one or more vias, the first portion and the second portion with solder material using injection molded soldering, and removing remaining portions of the first photoresist layer and the second photoresist layer.

DETAILED DESCRIPTION

Figure 1:
FIG. 1 depicts a side cross-sectional view of a substrate, according to an embodiment of the invention.

Illustrative embodiments of the invention may be described herein in the context of illustrative methods for filling trenches and/or vias using injection molded soldering (IMS), as well as illustrative apparatus, systems and devices having trenches and/or vias filled using IMS. However, it is to be understood that embodiments of the invention are not limited to the illustrative methods, apparatus, systems and devices but instead are more broadly applicable to other suitable methods, apparatus, systems and devices.

Various types of electronic and other devices utilize vias and/or trenches to form interconnects between different layers in a structure, between different functional features in the same layer, etc. A goal in fabrication of such devices is to make the devices smaller. As the devices themselves get smaller, it is also desired to shrink or reduce the size of any trenches or vias formed therein. As trenches and vias become smaller and smaller, it becomes more difficult to fill the trenches and vias using conventional techniques. For example, it may be desired to form trenches and/or vias with high aspect ratios. A high aspect ratio, for example, may be 15:1, e.g., 300 microns depth, 20 microns diameter and 50 microns pitch. Embodiments are not limited to vias having an aspect ratio of 15:1. More generally, embodiments provide advantages for filling trenches and/or vias with aspect ratios ranging from about 3:1 to 25:1 or greater. It is to be appreciated, however, that embodiments may be used with any sized via or trench regardless of its aspect ratio.

In addition to making electronic and other devices smaller, some electronic and other devices are beginning to use different materials which present challenges for filling vias and interconnects formed therein. As one example, the low resistivity of silicon can raise concerns relating to power consumption and noise coupling performance in various applications. In a WiFi system, for example, glass may be used in place of silicon for an interposer. Various other applications may utilize glass interposers and/or trenches or vias with a high aspect ratio, including but not limited to robotic devices, smart devices or tags, biological sensors, wearable sensors, radio frequency (RF) antennas, Internet of Things (IoT) devices, drug delivery patches, moisture proof or hermetic encapsulation sealing of heterogeneous structures, biocompatible and environmentally friendly devices, etc. Filling trenches or vias in glass, however, can be difficult particularly as the sizes of trenches and vias become smaller. A need therefore exists for techniques for via filled glass structures with long term reliability.

Some embodiments provide techniques for facilitating trench and/or via filling using IMS, as will be described below in the context of FIGS. 1-27. It is to be appreciated that FIGS. 1-27, for clarity of illustration, are not necessarily drawn to scale. In addition, it is important to note that the various example sizes and ranges given below when describing elements shown in FIGS. 1-27 are presented by way of example only. Embodiments are not limited solely to the examples given unless specifically noted otherwise below.

FIG. 1 shows a side cross-sectional view 100 of a substrate 102. The substrate 102 may be a glass substrate, a silicon substrate, a polymer substrate, a ceramic substrate, etc. The substrate 102 may also be referred to as a wafer herein. Polymer substrates include, by way of example, polyethylene terephthalate (PET), polyethylene-naphthalate (PEN), polyimide (PI), etc. Glass substrates may be, by way of example, fused quartz, fused silica, sapphire, Indium tin oxide (ITO), BOROFLOAT®, borosilicate, etc.

The substrate 102 can be a wafer with round shape, a panel with square or rectangular shape, or a continuous flexible film that is windable on rotating drums. Si and glass substrates, for example, may be wafers. Glass and polymer substrates can be panel substrates. Flexible substrates, such as polyimide layers, can be roll-to-roll substrates.

Figure 2A:
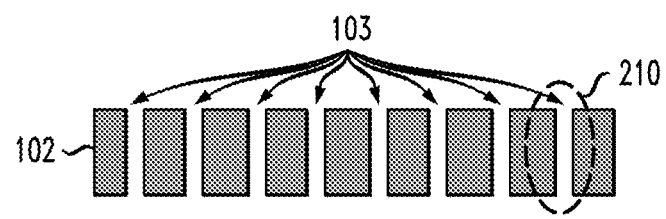
FIG. 2A depicts a side cross-sectional view of the FIG. 1 substrate following formation of vias, according to an embodiment of the present invention.

FIG. 2A shows a side cross-sectional view 200 of the substrate 102 following formation of vias 103 therein. Although FIG. 2A shows the vias 103 of uniform size, embodiments are not so limited as will be discussed in further detail below with respect to FIG. 7. In addition, the particular number of vias 103 that are formed in substrate 102 may vary depending on the needs of a particular device or application. Vias 103 may be blind vias which may be formed using backside grinding, etc. Depending on the material of the substrate 102, the vias 103 may be referred to as through-silicon vias (TSVs), through-glass vias (TGVs), etc. Vias 103 may be formed using various techniques, including but not limited to laser drilling, chemical etching, dry etching, mechanical machining, etc.

The substrate 102, in some embodiments, may be a 2 inch to 12 inch wafer, a 450 mm wafer, etc. The wafer may have a thickness ranging from 30 microns to 800 microns. Certain substrate materials, such as glass, may be a panel, such as a 500 mm×500 mm panel. The vias 103 may have a high aspect ratio. As described above, a high aspect ratio may be 15:1. In other embodiments, a high aspect ratio may be even higher, such as 25:1 or greater. Diameters of a high aspect ratio via may be, by way of example, as small as 5 μm. The vias 103 in some embodiments have a thickness ranging from 30 microns to 300 microns. Pitch range for vias 103 in some embodiments is 10 microns to 100 microns.

Figure 2B:
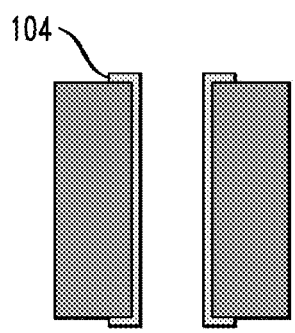
FIG. 2B depicts a close-up side cross-sectional view of one of the vias shown in the FIG. 2A substrate, according to an embodiment of the present invention.

FIG. 2B shows a close-up side cross-sectional view 210 of one of the vias 103 in the view 200. The view 210 shows one of the vias 103 having a liner 104 formed on the sidewalls thereof. The liner 104 may be one of or a combination of layers.

In some embodiments, the liner 104 comprises a solder adhesion layer. A solder adhesion layer may be formed from a metal that helps solder wetting and allows solder fill material to flow easily into the vias 103. The solder adhesion layer therefore improves solder filling yield for vias 103 having high aspect ratios. In particular, the use of a solder adhesion layer as the liner 104 may be useful in cases where the via 103 has a high aspect ratio of 5:1 or greater for both a Si substrate and a glass substrate, as it is difficult to fill such high aspect ratio through vias or blind vias due to lower solder flow/wetting in the through via or blind via. The solder adhesion layer, however, is not limited solely to use with vias having aspect ratios 5:1 or greater.

The solder adhesion layer may be formed from copper (Cu), gold (Au), chromium (Cr), tin (Sn), a copper-nickel (CuNi) alloy, a chromium-nickel-gold (CrNiAu) alloy, a chromium-nickel-copper-gold (CrNiCuAu) alloy, a titanium-nickel (TiNi) alloy, a titanium-copper-nickel-gold (TiCuNiAu) alloy, etc. The solder adhesion layer may have a thickness of 0.1 microns to 10 microns in some embodiments. The thickness of the solder adhesion layer may depend on the type of solder material used. For example, a high Sn percentage solder would benefit from a thicker adhesion layer.

In other embodiments, the liner 104 may be a barrier layer. Some substrate materials, such as silicon, are not attractive for high frequency RF applications due to the low resistivity of silicon. The low resistivity of silicon raises concerns about power consumption and noise coupling performance. These concerns may be at least partially reduced via the use of a barrier layer as the liner 104.

The barrier layer may be formed from nickel (Ni), titanium (Ti), molybdenum (Mo), titanium nitride (TiN), tantalum (Ta), tantalum nitride (TaN), etc. The barrier layer may have a thickness of 0.1 microns to 2 microns.

In some embodiments, the liner 104 may include both a barrier layer and a solder adhesion layer. For example, the liner 104 may include a barrier layer formed on sidewalls of one or more of the vias 103, and a solder adhesion layer formed over the barrier layer. In such embodiments, the thicknesses of the barrier layer and solder adhesion layer may be the same as that described above. Generally, the solder adhesion layer is formed thicker than the barrier layer but this is not a strict requirement.

The liner 104 may be formed using a variety of processing techniques, including but not limited to chemical vapor deposition (CVD), physical vapor deposition (PVD), atomic layer deposition (ALD), electroplating, electroless plating, etc.

The liner 104 provides enhanced reliability of the vertical structure. For example, the liner 104 may include a barrier layer and/or a solder adhesion bonding layer which advantageously prevents corrosion and/or excessive current flow. The liner 104 may be a TSV, a tantalum oxide liner, a titanium or nickel liner to vent the surface of the vias 103, etc. The liner 104 may be used as a barrier layer, a solder adhesion or bonding layer, etc.

Figure 3A:
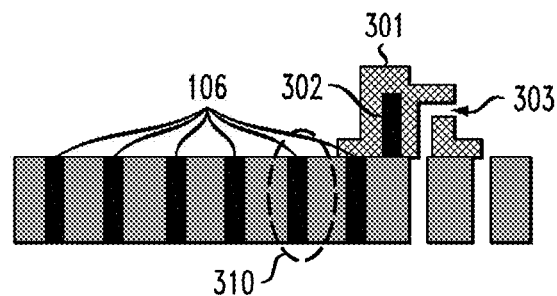
FIG. 3A depicts a side cross-sectional view of filling the plurality of vias in the FIG. 2A substrate, according to an embodiment of the present invention.

FIG. 3A shows a side cross-sectional view 300 of the substrate 102 as the vias 103 are filled using IMS. View 300 shows an IMS head 301, which includes solder material 302 and a vacuum 303. The IMS head 301 in this example sweeps left to right across the substrate, such that the vacuum 303 creates a vacuum in the vias 103 prior to depositing the solder material 302 into the vias 103. In other embodiments the IMS head 301 may sweep right to left, front to back, back to front, etc. As shown, several of the vias 103 in view 300 are filled with solder material 106. The solder material 106 may be, by way of example, tin (Sn), a tin-silver (SnAg) alloy, a tin-copper (SnCu) alloy, a tin-silver-copper (SnAgCu) alloy, indium (In), bismuth (Bi), an indium-tin (InSn) alloy, a bismuth-tin (BiSn) alloy, an indium-bismuth-tin (InBiSn) alloy, a gold-tin (AuSn) alloy etc.

Figure 3B:
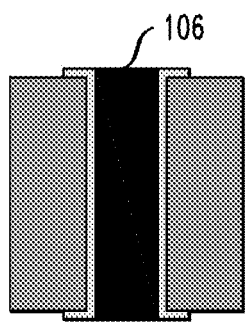
FIG. 3B depicts a close-up side cross-sectional view of one of the filled vias in the FIG. 3A substrate, according to an embodiment of the present invention.

FIG. 3B shows a close-up side cross-sectional view 310 of one of the filled vias 103 in the view 300. As shown in FIG. 3B, the solder material 106 fills the via, with the liner 104 facilitating the fill of the via by helping solder wetting to allow the solder material 302 from IMS head 301 to flow more easily into the via. The use of the liner 104 thus improves solder filling yield, while also providing benefits relating to corrosion effects and excess current flow.

Figure 4:
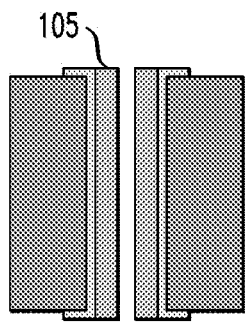
FIG. 4 depicts a close-up side cross sectional view of the FIG. 2B via following formation of a metal layer on the barrier layer, according to an embodiment of the present invention.

In some embodiments, techniques may be used to form an intermetallic compound (IMC) in one or more of the vias 103. FIG. 4 shows a close-up cross sectional view 400 of the via shown in FIG. 2B following formation of metal layer 105 on the liner 104. The metal layer 105 may be a copper (Cu) or nickel (Ni) layer, Au coated Cu, Au coated Ni, etc. The metal layer 105 may have a thickness that is based at least in part on the diameter of the via. For example, the total thickness of the metal layer 105 and liner 104 may range from approximately ½ to ¾ of the via diameter in some embodiments. As an example, the metal layer 105 may be 5 microns thick when the via diameter is 20 microns. When the metal layer 105 is Au-coated, the Au coating may have a thickness of approximately 0.1 to 1 micron.

Figure 5:
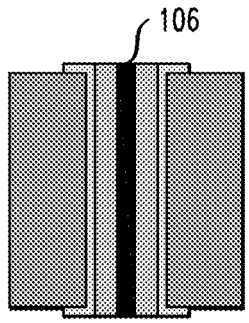
FIG. 5 depicts a close-up side cross sectional view of the filled FIG. 4 via, according to an embodiment of the present invention.

FIG. 5 shows a close-up side cross-sectional view 500 of the FIG. 4 via after it is filled with solder material 106 via IMS. In some embodiments, in the case of 20 microns diameter of via, the liner 104 may be 1 micron thick, the metal layer 105 may be 5 microns thick, and the solder material 106 may be 8 microns thick. It is to be appreciated, however, that these thickness are provided by way of example only and that embodiments are not limited solely to the use with this specific example thickness. The structure shown in FIG. 5 may be thermally annealed to form IMC 108 as shown in the close-up side cross-sectional view 600 in FIG. 6.

Figure 6:
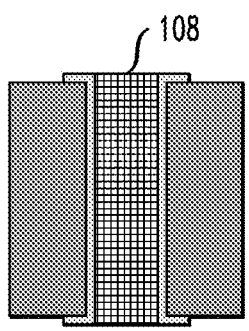
FIG. 6 depicts a close-up side cross-sectional view of the FIG. 5 via following a thermal annealing process, according to an embodiment of the present invention.

The thermal anneal process may use a time in the range of 30 minutes to 1 hour at a temperature over the melting temperature of solder material 106. As shown in FIG. 6, after formation of the IMC 108, at least a portion of the liner 104 remains. The amount of liner 104 which remains after the thermal anneal will depend on the specific annealing process, as well as the volume ratio between the solder material 106 and the liner 104. In some embodiments, at least a portion of the liner 104 may be the same material as the metal layer 105. The formation of IMC 108 is the result of reaction between the solder material 106 and the metal layer 105. For example, the solder material 106 and metal layer 105 may result from a reaction of Cu or Ni in the liner 104/metal layer 105 with Sn in the solder material 106. The IMC 108 may be $Cu_3Sn$ or $Cu_6Sn_5$ when the liner 104 is Cu, or $Ni_3Sn_4$ when the liner 104 is Ni. If the liner 104/metal layer 105 is thick, the Cu in the liner 104 will not totally react with the Sn in the solder material 106 and thus at least a portion of the liner 104 may remain after formation of IMC 108 even when the liner 104 and metal layer 105 are formed at least partially of the same material.

IMC 108 can be used to provide a number of benefits, including but not limited to providing an increased current carrying capacity. For example, if the solder material 106 is Sn and the liner 104 is Cu, the IMC 108 will be $Cu_6Sn_5$ and/or $Cu_3Sn$. The melting temperature of Sn is 232° C., but the melting temperature of $Cu_6Sn_5$ is 415° C. and the melting temperature of $Cu_3Sn$ is 676° C. The higher melting temperature of the IMC 108 provides an increased current carrying capacity.

Figure 7:
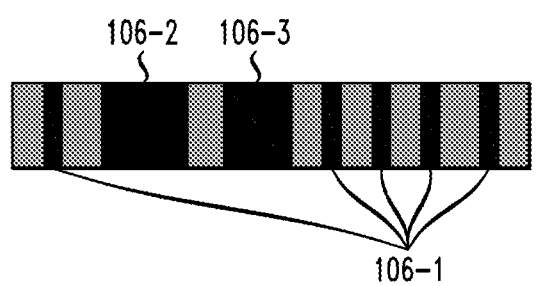
FIG. 7 depicts a side cross-sectional view of a substrate with filled vias wherein the filled vias have different thicknesses, according to an embodiment of the present invention.

As mentioned above, in some embodiments different ones of the vias 103 formed in substrate 102 may be different sizes. FIG. 7 shows a side cross-sectional view 700 of such a structure. FIG. 7 shows filled vias of three different sizes—solder filled vias 106-1, solder filled via 106-2 and solder filled via 106-3. It is to be appreciated that a single substrate may have only two different sized vias, or more than three different sized vias in other embodiments. In the FIG. 7 example, solder filled via 106-2 is approximately five times the thickness of solder filled vias 106-1, and solder filled via 106-3 is approximately three times the thickness of solder filled vias 106-1. It is to be appreciated, however, that these relative sizes are shown simply for clarity of illustration, and that vias may be different sizes that are not necessarily three times or five times the multiple of another via. The sizing of liner 104, solder adhesion layers and barrier layers may be the same regardless of the thickness of the vias used. For example, in some embodiments the liner 104 is the same size for solder-filled vias 106-1, 106-2 and 106-3.

Different size vias may be used for different purposes. For example, some vias may be used for interconnects between electrical components in different layers of a multi-layer structure, as will be described in further detail below with respect to FIGS. 14-16. Other vias may be filled so as to bond different layers in a multi-layer structure, as will also be described in further detail below with respect to FIGS. 14-16. In some embodiments, vias may be filled to seal different substrates together, as will be described in further detail below with respect to FIGS. 17-27. The purpose of a via (e.g., forming an interconnect, bonding layers together, forming a seal, etc.) may require different sized vias. Different interconnects may also require different thicknesses to provide different current flows between different types of functional features for a particular application. Various other examples are possible.

As mentioned above, some silicon interposers or substrates are not attractive for high frequency RF applications due in part to the low resistivity of silicon, which raises concerns relating to power consumption and noise coupling performance. Glass represents an alternative substrate or interposer material, which may be used as a building block for mobile integration on interposers. Glass provides a number of desirable properties, including low substrate losses in the RF/microwave range, mechanical robustness, and low material and manufacturing cost. Using the above-described techniques for IMS via filling, it is possible to further reduce the costs associated with using glass for interposers.

Glass interposers may be used, by way of example, as part of a WiFi system. WiFi baseband (BB) and RF components, along with an antenna, may be formed on a glass interposer. Vias or trenches formed in the glass interposer may be used to form interconnects between WiFi BB and RF components as well as the antenna. As an example, the above-described techniques may be used to form a 1 mm ground-signal-ground (GSG) transmission line between the WiFi RF component and an antenna running at 60 GHz with power loss at 14%, compared with a power loss of 26.7% using a silicon interposer. Thus, the glass interposer represents a 48% improvement over using the silicon interposer. It is to be appreciated, however, that in some cases silicon interposers may be used for WiFi systems and other high frequency RF applications. The use of the barrier layer in liner 104, for example, can at least partially reduce the concerns relating to silicon's low resistivity.

In some embodiments, using techniques described above with respect to FIGS. 1-7, a method includes forming one or more vias in a substrate, forming at least one liner on at least one sidewall of at least one of the vias, and filling said at least one via with solder material using injection molded soldering. The at least one via may have a high aspect ratio, such as an aspect ratio of 3:1 or greater, 15:1 or greater, 25:1 or greater, etc. Forming one or more vias in the substrate may include forming at least a first via having a first thickness and forming at least a second via having a second thickness different than the first thickness. Forming the at least one liner may include forming at least a first liner on at least one sidewall of the first via and forming at least a second liner on at least one sidewall of the second via.

The substrate may be formed of various materials. For example, the substrate may comprise a glass substrate, and the liner may comprise a solder adhesion layer. The solder adhesion layer may comprise at least one of a copper layer, a nickel layer, a chromium layer, a gold layer and a titanium layer. The solder adhesion layer may have a thickness that is independent of the size of the at least one via.

As another example, the substrate may comprise a silicon substrate and the liner may comprise a barrier layer and a solder adhesion layer formed over the barrier layer. The barrier layer may comprise at least one of a nickel layer, a titanium layer, a titanium nitride layer, a tantalum layer and a tantalum nitride layer with the solder adhesion layer comprising at least one of a copper layer, a nickel layer, a chromium layer, a gold layer and a titanium layer. The barrier layer may have a first thickness and the solder adhesion layer may have a second thickness, where the second thickness is greater than the first thickness.

The liner may be formed by forming a barrier layer, forming a solder adhesion layer on the barrier layer and forming a metal layer on the solder adhesion layer. In some cases, the solder adhesion layer and the metal layer may be the same. The metal layer may comprise one of copper, gold, and nickel. The total thickness of the liner, including the barrier, layer, solder adhesion layer and metal layer, may be approximately ½ to ¾ of the diameter of the at least one via. The filled via may be thermally annealed so as to form an intermetallic compound from the metal layer and the solder.

An apparatus, formed using the above-described method, may include a substrate having one or more vias formed therein, wherein at least one of the vias has at least one liner formed on at least one sidewall thereof, and one or more interconnects formed through said at least one via, the interconnect comprising solder material filled using injection molded soldering. As described above, the substrate may be a glass substrate and the liner may be a solder adhesion layer. The substrate may alternatively be a silicon substrate, and the liner may include a barrier layer and a solder adhesion layer formed over the barrier layer. A barrier layer may also be part of the liner used for a glass substrate in some embodiments. A first one of the vias in the substrate may have a first thickness and a second one of the vias in the substrate may have a second thickness different than the first thickness.

An integrated circuit may also be formed using the above-described method. For example, such an integrated circuit may include a glass interposer having one or more vias formed therein, wherein at least one of the vias has a solder adhesion layer formed on at least one sidewall thereof, and at least one interconnect formed through said at least one via, the interconnect comprising solder material filled using injection molded soldering.

In some embodiments, IMS is used to fill vias and provide electrical connections at the same time. An exemplary process for doing so will be described in detail below with respect to FIGS. 8-13.

Figure 8:
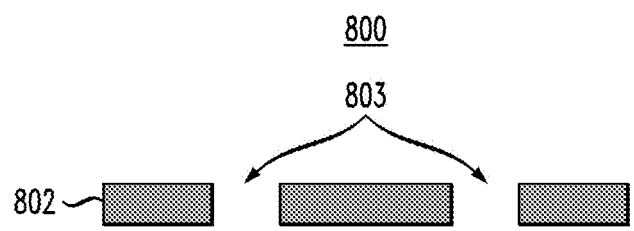
FIG. 8 depicts a side cross-sectional view of a substrate with vias formed therein, according to an embodiment of the present invention.

FIG. 8 shows a side cross-sectional view 800 of a substrate 802 having vias 803 formed therein. The vias 803 may be formed using processes similar to those used in forming vias 103 in substrate 102 as discussed above. The substrate 802, similar to the substrate 102, may be formed of various materials including but not limited to glass, silicon, ceramic, a polymer, etc.

Substrate 802 may be sized similar to the substrate 102 described above. Vias 803, similar to the vias 103, may vary in size as needed for a particular application. In some embodiments, the vias 803 are dimensioned similar to the vias 103 described above.

Figure 9:
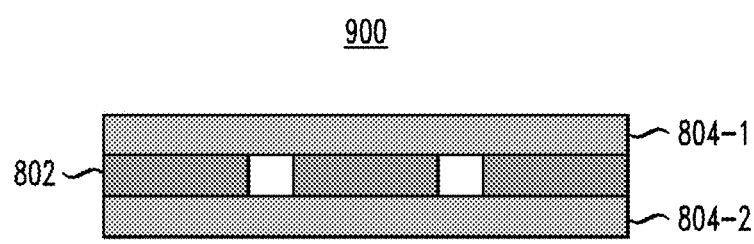
FIG. 9 depicts a side cross-sectional view of the FIG. 8 substrate following formation of photoresist layers on the top and bottom surfaces of the FIG. 8 substrate, according to an embodiment of the present invention.

FIG. 9 shows a side cross-sectional view 900 of the substrate 802 with photoresist layers 804-1 and 804-2 formed on a top and bottom surface thereof. The photoresist layers 804-1 and 804-2 are next patterned as shown in the cross-sectional view 1000 of FIG. 10. Various techniques may be used for patterning the photoresist, including but not limited to ultraviolet (UV) exposure, photolithography, etc.

Figure 10:
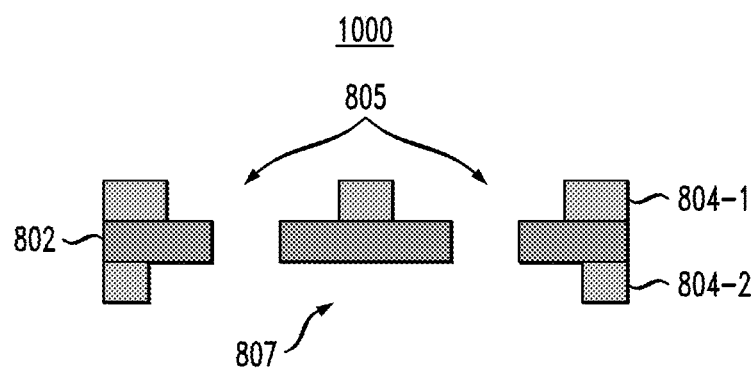
FIG. 10 depicts a side cross-sectional view of the FIG. 9 substrate following patterning of the photoresist layers, according to an embodiment of the present invention.

As shown in FIG. 10, the top photoresist layer 804-1 is patterned so as to expose regions 805 while the bottom photoresist layer 804-2 is patterned so as to expose region 807. It is to be appreciated, however, that the particular patterning of the photoresist layers 804-1 and 804-2 may vary depending on the needs of a particular application. By way of example, in some embodiments the patterning of the top and bottom photoresist layers 804-1 and 804-2 may be the same size and shape and aligned with one another—in other words the same portions of the top and bottom surfaces of the substrate 802 may be exposed instead of the differing exposed portions as shown in FIG. 10.

Although not explicitly shown in FIGS. 8-10, a liner similar to liner 104 may be formed on sidewalls of one or more of the vias 803 of substrate 802. Thus, the techniques described above with respect to FIGS. 1-7, including forming liners having solder adhesion layers, barrier layers, metal layers for formation of IMCs, etc. may be used for the vias 803 in substrate 802.

Figure 11:
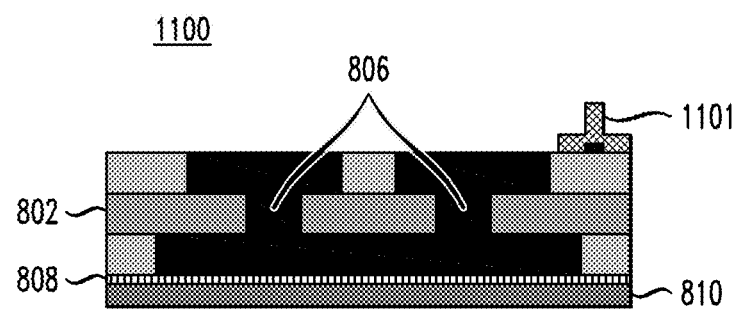
FIG. 11 depicts a side cross-sectional view of filling vias in the FIG. 10 substrate, according to an embodiment of the present invention.

FIG. 11 shows a side cross-sectional view 1100 of filling the vias 803 in substrate 802 using IMS head 1101. As shown, the FIG. 10 structure is placed on a plate 810 having an oxide layer 808 formed on a top surface thereof. The plate 810 may be a rigid or flexible layer where molten solder is not wetting. As an example, the plate 810 may be a Kapton® or other polyimide film, glass, or a Si wafer with a natural Si-oxide on its surface. The oxide layer 808 ensures non-wetting of solder material from IMS head 1101 as it sweeps from left to right across the top surface of the photoresist layer 804-1. The vias 803 are filled with solder material 806, as are the exposed portions of the photoresist layers 804-1 and 804-2. Liners may be used as described above with respect to FIGS. 1-7 to facilitate the solder fill process.

Figure 12:
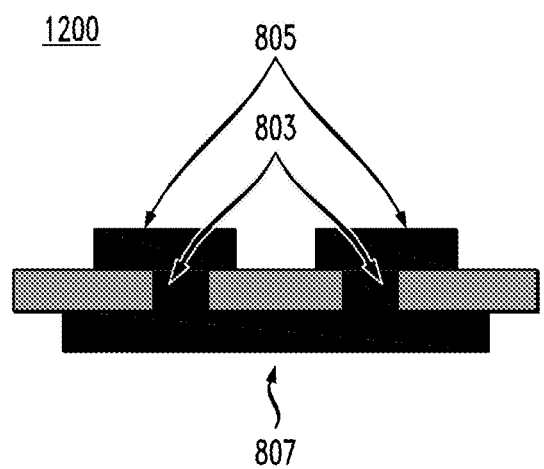
FIG. 12 depicts a side cross-sectional view of the FIG. 11 substrate following removal of the remaining photoresist layers, according to an embodiment of the present invention.

The remaining portions of the photoresist layers 804-1 and 804-2 may then be removed, and the resulting structure is shown in the side cross-sectional view 1200 of FIG. 12. FIG. 12 also shows the resulting structure removed from the plate 810 and oxide layer 808.

Figure 13:
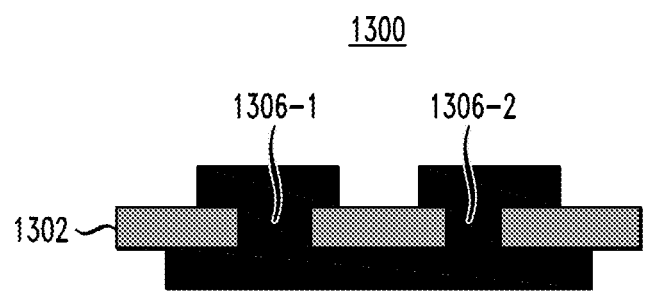
FIG. 13 depicts a side cross-sectional view of the FIG. 12 substrate wherein different filled vias have different thicknesses, according to an embodiment of the present invention.

While FIGS. 8-12 show a substrate 802 having vias 803 that are the same size, embodiments are not limited to this arrangement. FIG. 13 shows a side cross-sectional view 1300 of a substrate 1302 with filled vias and interconnects 1306-1 and 1306-2. As shown, the via formed in substrate 1302 of the filled via and interconnect 1306-1 is approximately twice the thickness of the via formed in substrate 1302 of the filled via an interconnect 1306-2. Various other arrangements are possible, including substrates with more than two vias formed therein, as well as substrates with more than two different sized vias formed therein.

The use of IMS to fill the vias 803 and exposed portions of the photoresist layer 804-1 and 804-2 provides a number of advantages, including simplifying the fabrication process by forming filled vias and connections at the same time, rather than via multiple depositions, photolithography, and etchings. Using IMS, the time for filling vias is the same regardless of the thickness of the via and connections. In contrast, using electroplating the plating time is dependent on the size and thickness of vias and connections. The bigger and thicker the vias and/or connection, the more time is needed for plating processes. Also, in the resulting structure shown in FIG. 12, the filled vias 803 are connected via the solder material formed in the region 807 and individual ones of the vias may interconnect to other components via the solder material formed in regions 805.

In some embodiments, using techniques described above with respect to FIGS. 8-13, a method includes forming one or more vias in a substrate, forming a first photoresist layer on a top surface of the substrate and a second photoresist layer on a bottom surface of the substrate, patterning the first photoresist layer and the second photoresist layer to remove at least a first portion of the first photoresist layer and at least a second portion of the second photoresist layer, filling the one or more vias, the first portion and the second portion with solder material using injection molded soldering, and removing remaining portions of the first photoresist layer and the second photoresist layer. The substrate may be, for example, a glass substrate or a silicon substrate. At least one of the vias may have a high aspect ratio, such as an aspect ratio of 3:1 or greater, 15:1 or greater, 25:1 or greater, etc.

Patterning the first photoresist layer may form at least a first exposed portion of the top surface of the substrate and patterning the second photoresist layer may form at least a second exposed portion of the bottom surface of the substrate. The first exposed portion of the top surface of the substrate and the second exposed portion of the bottom surface of the substrate may be the same size, the same shape, and aligned with one another in some embodiments. In other embodiments, the first exposed portion of the top surface of the substrate and the second exposed portion of the bottom surface of the substrate are at least one of different sizes, different shapes and not aligned with one another.

Patterning the first photoresist layer may form at least two distinct exposed portions of the top surface of the substrate. The two distinct exposed portions of the top surface of the substrate may be different sizes and/or different shapes in some embodiments. In other embodiments two or more of such distinct exposed portions are a same size, same shape, or both the same size and the same shape.

Forming the one or more vias in the substrate may comprise forming a first via having a first thickness and forming a second via having a second thickness different than the first thickness. Filling the one or more vias may comprise placing the second photoresist layer over an oxide layer formed on an additional substrate, filling the one or more vias, the first portion and the second portion with the solder material using injection molded soldering, and removing the oxide layer and the additional substrate.

At least one liner may be formed on at least one sidewall of at least one of the vias, such as using techniques described above with respect to FIGS. 1-7. For example, the substrate may comprise a glass substrate and the at least one liner may comprise a solder adhesion layer. The substrate may also be a silicon substrate, and the at least one liner may comprise a barrier layer and a solder adhesion layer formed over the barrier layer. Forming the at least one liner may include forming a solder adhesion layer and forming a metal layer on the solder adhesion layer. The filled via may be thermally annealed so as to form an intermetallic compound from the metal layer and the solder material deposited using injection molded soldering.

An apparatus may be formed using the methods described above, with the apparatus comprising a substrate having one or more vias formed therein and one or more interconnects formed through respective ones of the one or more vias, wherein at least one of the interconnects extends from a top surface of the substrate through at least one of the vias to a bottom surface of the substrate. The at least one interconnect may comprise a first portion formed on the top surface of the substrate surrounding the at least one via, a second portion formed on the bottom surface of the substrate surrounding the at least one via, and a third portion connecting the first portion and the second portion. The first portion, the second portion and the third portion comprise solder material filled using injection molded soldering. The substrate may be a glass substrate, and at least one liner may be formed on a sidewall of the at least one via.

An integrated circuit may also be formed using the above-described method. For example, such an integrated circuit may include a glass interposer having one or more vias formed therein and one or more interconnects formed through respective ones of the one or more vias. At least one of the interconnects extends from a top surface of the glass interposer through at least one of the vias to a bottom surface of the glass interposer. The at least one interconnect comprises a first portion formed on the top surface of the glass interposer surrounding said at least one via, a second portion formed on the bottom surface of the glass interposer surrounding said at least one via, and a third portion connecting the first portion and the second portion, wherein the first portion, the second portion and the third portion comprise solder material filled using injection molded soldering.

Figure 14:
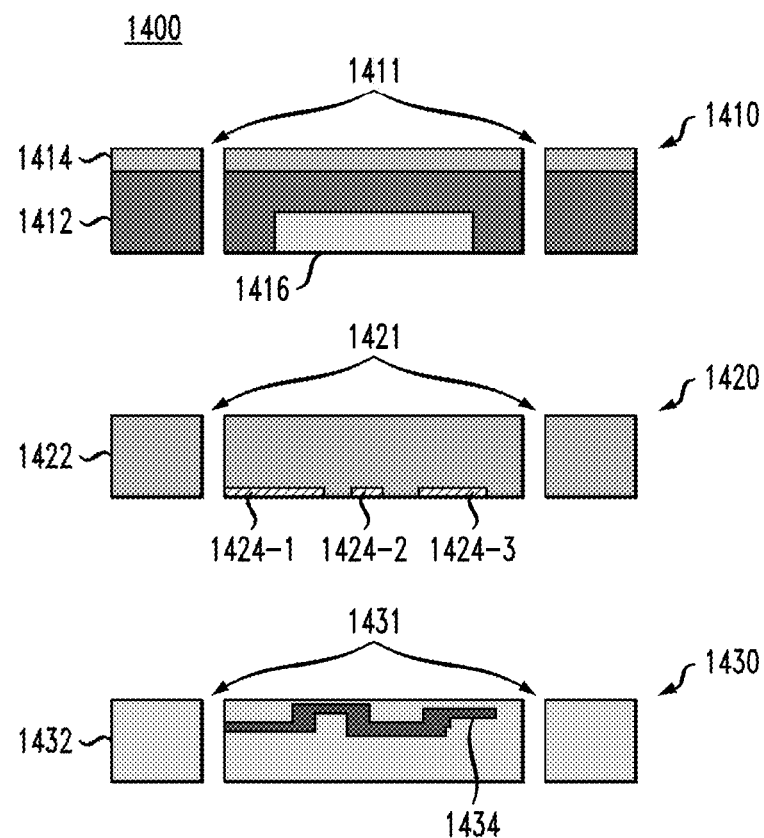
FIG. 14 depicts a side cross-sectional view of three heterogeneous layers having respective vias formed therein, according to an embodiment of the present invention.
Figure 15:
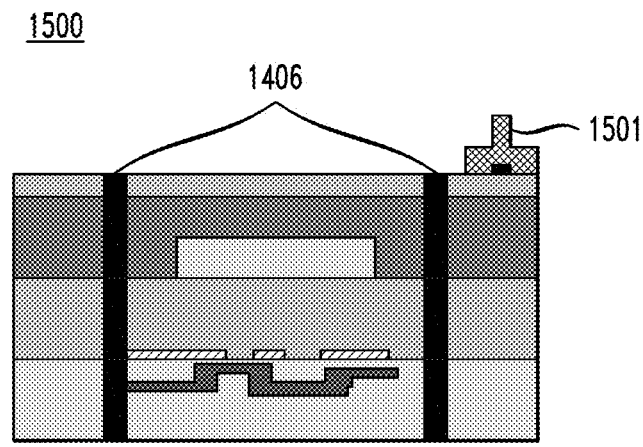
FIG. 15 depicts a side cross-sectional view of the three heterogeneous layers of FIG. 14 bonded together by filling the vias, according to an embodiment of the present invention.
Figure 16:
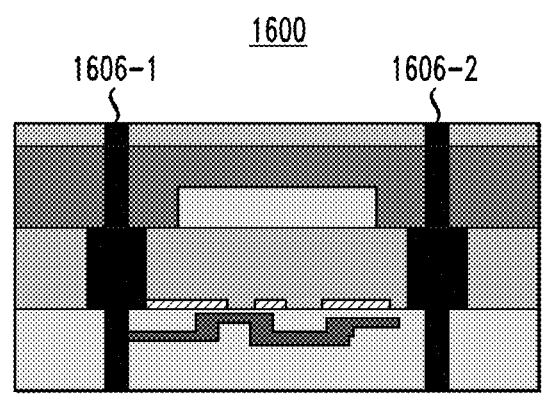
FIG. 16 depicts a side cross-sectional view of heterogeneous layers bonded together by filling vias formed therein with the vias in the heterogeneous layers having different thicknesses, according to an embodiment of the present invention.

In some embodiments, IMS may be used to bond and connect different layers via vias formed in the different layers. FIGS. 14-16 show an example process for using IMS to bond and connect heterogeneous layers.

FIG. 14 shows a side cross-sectional view 1400 of three heterogeneous layers 1410, 1420 and 1430. Layer 1410 includes a molding compound 1412 and an antenna 1414 formed over the molding compound. The molding compound 1412 may be, by way of example, an epoxy mixed with SiO$_2$ particles while the antenna may be a copper thin film. The molding compound 1412 may be 450 microns thick, or more generally in the range of 50-800 microns in some embodiments. The antenna 1414 may be 1-10 microns thick in some embodiments. Layer 1410 also includes a silicon device 1416 embedded in the molding compound 1410. The silicon device 1416 may be, by way of example, a microprocessor, memory, etc. The silicon device 1416 may range in size from 1 mm width and 20 microns height to 10 mm width and 300 microns height in some embodiments. As shown, vias 1411 are formed through the layer 1410. The vias 1411 may be similar in size to the vias 103 described above.

Layer 1420 includes an interposer 1422, which may be formed of glass, silicon, a polymer, etc. The interposer 1422 may have a thickness ranging from 20-100 microns in some embodiments. Embedded passives 1424-1, 1424-2 and 1424-3 are formed in the interposer 1422. The embedded passives 1424-1, 1424-2 and 1424-3 may be respective capacitors, resistors, inductors, etc. As shown vias 1421 are formed through the layer 1420. The vias 1421 may be similar in size to vias 103 described above. In this embodiment, the embedded elements 1424-1, 1424-2 and 1424-3 are passive while the silicon device 1416 is active. Other arrangements of active and passive devices are possible in other embodiments. The embedded elements 1424-1, 1424-2 and 1424-3 may vary in size, from 1 mm width and 20 microns height to 10 mm width and 300 microns height in some embodiments.

Layer 1430 includes an organic substrate 1432. The organic substrate 1432 may be, by way of example, a bismaleimide triazine (BT) laminate with copper metal layers in some embodiments. Other suitable materials may also be used. The organic substrate 1432 may have a thickness in the range of 50-300 microns in some embodiments. As shown vias 1431 are formed through the layer 1430. The vias 1431 may be similar in size to vias 103 described above. The organic substrate 1432 includes an embedded component 1434. The embedded component 1434 may be a biological sensor, a battery, a gas sensor, etc. The embedded component 1434 may vary in size from 0.1 mm width and 1 microns height to 5 mm width and 100 microns height in some embodiments.

Although FIG. 14 shows an example wherein the sizes of the layers 1410, 1420 and 1430 are substantially the same, embodiments are not so limited. For example, the height of the layer 1410 may be greater or smaller than the height of layer 1420, which may be greater or smaller than the height of layer 1430 in other embodiments. In addition, although FIG. 14 shows an arrangement wherein the vias 1411 in layer 1410, the vias 1421 in layer 1420 and the vias 1431 in layer 1430 are the same thickness, embodiments are not so limited. In other embodiments, different ones of the layers 1410, 1420 and 1430 may have vias of different thicknesses relative to one another. One or more of the layers 1410, 1420 and 1430 may also include vias of different thickness internal to that layer. For example, the layer 1420 may include one via of a first thickness and a second via of a second thickness different than the first thickness.

In some embodiments, the different layers 1410, 1420 and 1430 may be purchased with the vias 1411, 1421 and 1431 pre-drilled or formed therein. In other embodiments the vias 1411, 1421 and 1431 may be formed after purchasing or otherwise obtaining the different layers.

The diameter or width of the overall multilayer structure shown in FIG. 14 may be approximately 300 mm in wafer, panel or roll form.

FIG. 15 shows a side cross-sectional view 1500 of the layers 1410, 1420 and 1430 bonded together via solder material 1406 deposited in the vias 1411, 1421 and 1431 via IMS head 1501 as the IMS head 1501 sweeps across the top surface of layer 1410. Although not explicitly shown in FIG. 14, liners such as liner 104 described above with respect to FIGS. 1-7 may be formed on the sidewalls of one or more of the vias 1411, 1421 and 1431. The techniques described above with respect to FIGS. 4-6 may also be used to form IMCs in the vias 1411, 1421 and 1431. The solder material 1406 can provide multiple functions and advantages. For example, the solder material 1406 filled via IMS can bond the layers 1410, 1420 and 1430 together. The solder material 1406 in filled vias 1411, 1421 and 1431 can also form interconnects in the resulting structure. By way of example, the solder material 1406 in filled vias 1411, 1421 and 1431 may provide interconnects between functional features in the layers 1410, 1420 and 1430, such as interconnecting the antenna 1424 to the embedded passive 1424-1 and the biological sensor 1434.

As shown in the side cross-sectional view 1600 of FIG. 16, the vias 1411, 1421 and 1431 in layers 1410, 1420 and 1430 need not be the same size. FIG. 16 shows an example wherein the middle layer (e.g., 1420) has thicker vias than the top layer (e.g., 1410) and the bottom layer (e.g., 1430). In some cases, the difference in via thickness may be a result of different manufacturing processes in the heterogeneous layers. In other embodiments, the difference in via thickness may be designed for a particular application, such as providing increased current carrying capacity through one or more layers in a heterogeneous structure.

The use of IMS-filled vias to bond layers provides a number of benefits and advantages. For example, the use of IMS-filled vias facilitates heterogeneous integration, useful in forming various types of devices including but not limited to biosensors, gas sensors, batteries, IoT devices, robotic devices, smart devices or tags, etc. The resulting bonding between layers may also be stronger using IMS than using other techniques. For example, solder material may have more ductility than electroplated Cu, thus providing better drop reliability.

In some embodiments, using techniques described above with respect to FIGS. 14-16, a method includes forming one or more vias in a first layer, forming one or more vias in at least a second layer different than the first layer, aligning at least a first via in the first layer with at least a second via in the second layer, and bonding the first layer to the second layer by filling the first via and the second via with solder material using injection molded soldering. The first layer may comprise a first substrate of a first material and the second layer may comprise a second substrate of a second material different than the first material. The first material may comprise a molding compound and the second material may comprise one of silicon and glass. Alternatively, the first material may comprise an organic substrate and the second material may comprise one of silicon and glass. In some cases, the first via and the second via have a same thickness, while in other embodiments their thicknesses may differ from one another.

The filled first and second via form an interconnect between at least a first functional feature in the first layer and at least a second functional feature in the second layer. The first functional feature may comprise an antenna and the second functional feature may comprise an embedded passive component. The embedded passive component may be a capacitor, resistor, inductor, etc. The first functional feature may alternatively be an antenna while the second functional feature is a biological sensor, a battery, etc.

In some embodiments, one or more vias may be formed in a third layer different than the first layer and the second layer. In such cases, aligning the first via in the first layer with the second via in the second layer further also includes aligning at least a third via in the third layer with the first via in the first layer and the second via in the second layer. Bonding the first layer to the second layer further includes bonding the first layer to the second layer and bonding the second layer to the third layer by filling the first via, the second via and the third via with solder material using injection molded soldering. The first layer may comprise a first substrate of a first material, the second layer may comprise a second substrate of a second material different than the first material, and the third layer may comprise a third substrate of a third material different than the first material and the second material. For example, the first material may be a molding compound, the second material may be one of silicon and glass, and the third material may be an organic substrate. In other cases, at least two of the first, second and third layers may be formed of the same material type. The filled first, second and third vias may form an interconnect between functional features in different ones of the layers, e.g., a first functional feature in the first layer and a second functional feature in the second layer, a first functional feature in the first layer and a second functional feature in the third layer, a first functional feature in the second layer and a second functional feature in the third layer, etc.

One or more vias in the first layer, second layer, and/or third layer may have a liner formed on at least one sidewall thereof using techniques described above with respect to FIGS. 1-7. For example, the liner may be a barrier layer and/or a solder adhesion layer.

An apparatus formed using the above-described method may have a first layer having one or more vias formed therein and at least a second layer having one or more vias formed therein. At least a first via in the first layer is aligned with at least a second via in the second layer and the first layer and the second layer are bonded together via solder material filling the first via and the second via, the solder material being filled using injection molded soldering. The first layer may comprise a first substrate of a first material and the second layer may comprise a second substrate of a second material different than the first material, with one of the first material and the second material being glass.

An integrated circuit may also be formed using the above-described method. For example, such an integrated circuit may include a first layer having one or more vias formed therein and at least a second layer having one or more vias formed therein. At least a first via in the first layer is aligned with at least a second via in the second layer and the first layer and the second layer are bonded together via solder material filling the first via and the second via, the solder material being filled using injection molded soldering. One of the first layer and the second layer may comprise a glass interposer.

In some embodiments, IMS is used to fill trenches and/or vias in two or more substrates so as to seal the two or more substrates together. FIGS. 17-27 illustrate processes for forming seals between substrates using IMS-filled trenches and vias.

Figure 17:
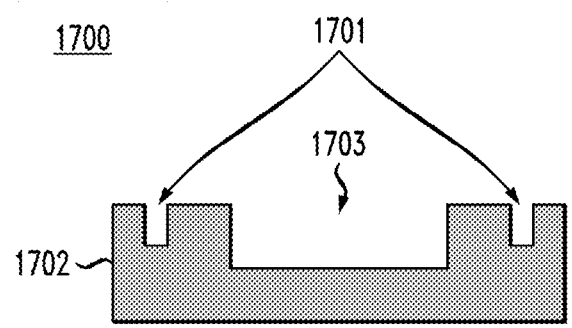
FIG. 17 depicts a side cross-sectional view of a bottom substrate having trenches formed therein, according to an embodiment of the present invention.

FIG. 17 shows a side cross-sectional view 1700 of a bottom substrate 1702. The bottom substrate 1702 may be silicon, glass, ceramic, a polymer material, etc. As shown, the bottom substrate has trenches 1701 and a reservoir 1703 formed therein. The trenches 1701 may be similar in size to the vias 103 described above. The size of the bottom substrate 1702 may range from 1 mm width and 20 microns height to 10 mm width and 300 microns height in some embodiments. The reservoir 1703 may vary in size from 0.5 mm width and 10 microns height to 5 mm width and 150 microns height in some embodiments. The trenches 1701 may be etched using laser drilling, dry etching, chemical etching, etc. The trenches 1701 are an example of a blind via.

The reservoir 1703 is formed to accept a delivery substance. While various embodiments are described below with respect to the delivery substance being a medical substance or drug, embodiments are not limited to the delivery substance being a medical substance. In other embodiments, the delivery substance may be a biosensor, gas sensor, battery, smart tag or other electronic device, etc. Depending on the type of delivery substance used, the top substrate 1902 and the bottom substrate 1702 may be pre-sterilized. The sterilization process may be achieved through the use of thermal insulator layers, as will be described in further detail below. Sterilization may be useful in cases when the delivery substance 1704 is sensitive at high temperature bonding.

Figure 18A:
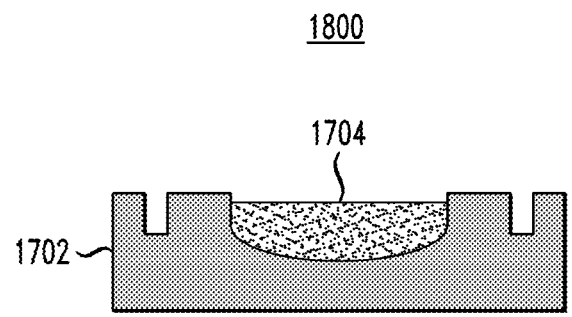
FIG. 18A depicts a side cross-sectional view of the FIG. 17 bottom substrate following formation of a delivery substance in one of the trenches, according to an embodiment of the present invention.

FIG. 18A shows a side cross-sectional view 1800 of the substrate 1702 after the delivery substance 1704 has been deposited in the reservoir 1703. As mentioned above, it will be assumed for purposes of illustration that the delivery substance 1704 is a medical substance or drug. As shown in FIG. 18A, the delivery substance 1704 does not completely fill the reservoir 1703. In other embodiments, however, the delivery substance 1704 may completely fill the reservoir 1703. In some cases, the delivery substance 1704 may protrude above the top surface of the substrate 1704.

Figure 18B:
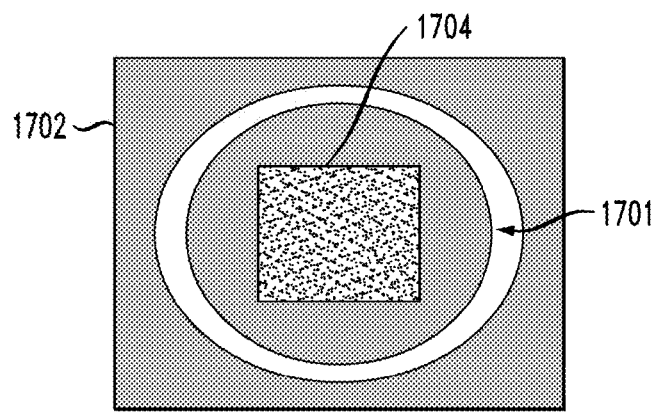
FIG. 18B depicts a top view of the FIG. 18A bottom substrate, according to an embodiment of the present invention.

FIG. 18B shows a top view 1850 of the FIG. 18A bottom substrate. As shown the trench 1701 surrounds the reservoir 1703 containing the delivery substance 1704. Although the trench 1701 is shown in the view 1850 as being circular, this is not a requirement. In other embodiments, the trench 1701 may be rectangular or some other shape which surrounds the reservoir 1703.

Figure 19:
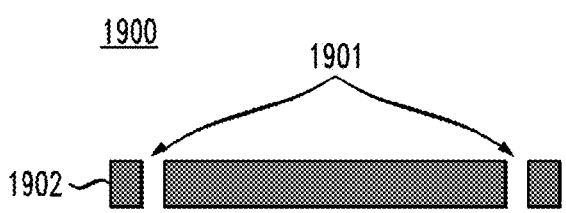
FIG. 19 depicts a side cross-sectional view of a top substrate having vias formed therein, according to an embodiment of the present invention.

FIG. 19 shows a side cross-sectional view 1900 of a top substrate 1902 having vias 1901 formed therein. The top substrate 1902 may be Si, glass, polymer, polyimide, etc. The vias 1901 may be formed using laser drilling, chemical etching, dry etching, etc. The vias 1901 may be similar in size to the vias 103 described above. The top substrate 1902 may range in size from 1 mm width and 10 microns height to 10 mm width and 300 microns height in some embodiments. The structure shown in view 1900 may be viewed as a cap that seals the delivery substance 1704 in the reservoir 1703 when the vias 1901 of the top substrate 1902 and the trenches 1701 of the bottom substrate are filled with solder material via IMS. As mentioned above, in some cases the delivery substance 1704 may protrude above a top surface of the reservoir 1703 formed in bottom substrate 1702. In such cases a matching recess or reservoir may be formed in the bottom surface of the top substrate 1902 to accommodate the portion of the delivery substance 1704 that protrudes above the top surface of the bottom substrate 1702.

Figure 20:
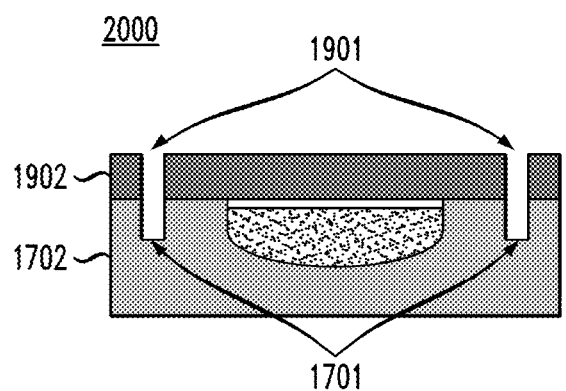
FIG. 20 depicts a side cross-sectional view of the top substrate of FIG. 19 aligned with the bottom substrate of FIG. 18A, according to an embodiment of the present invention.

FIG. 20 shows a side cross-sectional view 2000 of the top substrate 1902 aligned with the bottom substrate 1702. More particularly, the view 2000 shows that the vias 1901 of the top substrate 1902 are aligned with the trenches 1701 of the bottom substrate 1702. Although FIG. 20 and other ones of the figures show that the vias 1901 and trenches 1701 have matching or similar thicknesses, embodiments are not limited to this arrangement as will be discussed in further detail below with respect to FIG. 22.

Figure 21A:
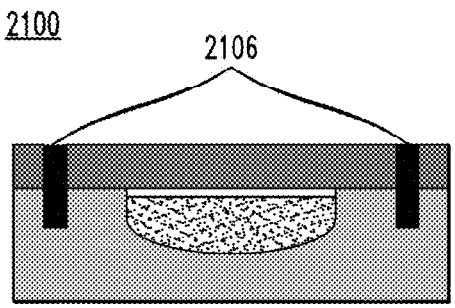
FIG. 21A depicts a side cross-sectional view of the aligned FIG. 20 structure following filling the vias and trenches to seal the top substrate of FIG. 19 to the bottom substrate of FIG. 18A, according to an embodiment of the present invention.
Figure 21B:
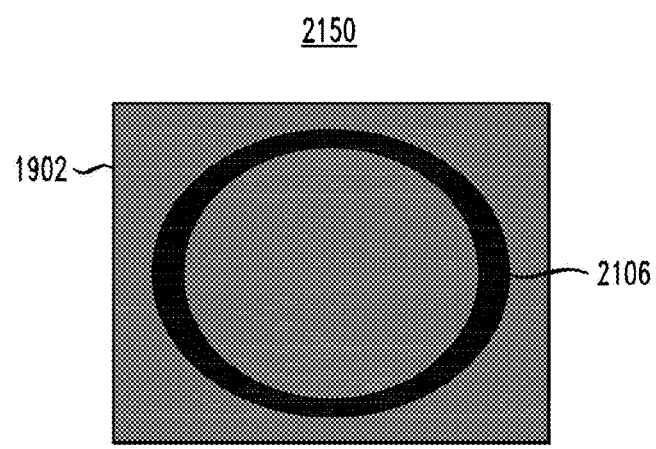
FIG. 21B depicts a top view of the FIG. 21A structure, according to an embodiment of the present invention.

FIG. 21A shows a side cross-sectional view 2100 of the FIG. 20 structure following fillings of the vias 1901 and trenches 1701 with solder material 2106 via IMS. The solder material 2106 seals the top substrate 1902 to the bottom substrate 1702, forming a cavity in the space where the reservoir 1703 aligns with the bottom surface of the top substrate 1902. Thus, the delivery substance 1704 is sealed therein. FIG. 21B shows a top view 2150 of the FIG. 21A structure.

Figure 22:
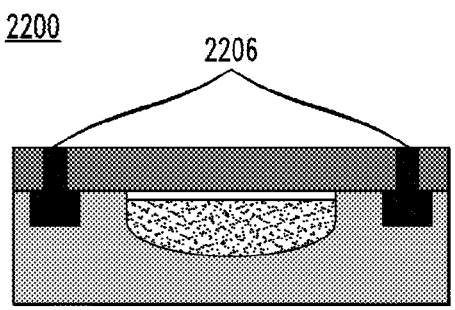
FIG. 22 depicts a side cross-sectional view of a top substrate sealed to a bottom substrate, wherein vias in the top substrate and trenches in the bottom substrate have different thicknesses, according to an embodiment of the present invention.

FIG. 22 shows a side cross-sectional view 2200 of the top substrate 1902 sealed to the bottom substrate 1702 via solder fill material 2206. More particularly, FIG. 22 illustrates an embodiment wherein the trenches formed in the bottom substrate 1702 are larger than the vias formed in the top substrate 1902. In other cases, however, the vias in the top substrate 1902 may be larger than the trenches formed in the bottom substrate 1702. In still other cases, one or both of the top substrate 1902 and the bottom substrate 1702 may have vias or trenches formed therein of different sizes.

Although not explicitly shown in FIGS. 17-22, a liner similar to liner 104 may be formed on sidewalls of one or more of the vias 1901 of top substrate 1902 and/or on sidewalls of one or more of the trenches 1701 of the bottom substrate 1702. Thus, the techniques described above with respect to FIGS. 1-7, including forming liners having solder adhesion layers, barrier layers, metal layers for formation of IMCs, etc. may be used for the vias 1901 in the top substrate 1902 and/or for the trenches 1701 of the bottom substrate 1702.

In addition to providing a seal between the top substrate 1902 and the bottom substrate 1702, the solder fill material 2106/2206 may be used to dispense the delivery material 1704 that is sealed in the cavity between the top substrate 1902 and the bottom substrate 1702. For example, the top substrate 1902 may be "blown" off to dispense the delivery substance 1704 by passing current through the solder fill material 2106/2206. The solder fill material 2106/2206 in such embodiments should have a relatively low melting temperature. For example, an InBiSn solder, with a 60° C. melting point, is a suitable solder material for such embodiments although other solder materials with low melting temperatures may be used. In such cases, the top substrate 1902 may be very thin, to facilitate delivery of the delivery substance 1704. As an example, the top substrate 1902 may be 5-50 microns thick. The thickness of the bottom substrate 1702 may vary as need so as to form a large enough reservoir 1703 to contain the delivery substance 1704.

In some embodiments, an additional layer is formed between the cavity and the remainder of the FIG. 21 or FIG. 22 structure. The additional layer may be used to protect the delivery substance placed in the reservoir from further processing steps. For example, the heat required to fill the trenches 1701 and vias 1901 with the solder fill material 2106/2206 may, in some cases, damage the delivery substance 1704. In other cases, the current applied to the solder fill material 2106/2206 to release the delivery substance 1704 or otherwise break the seal between the top substrate 1902 and bottom substrate 1702 may damage the delivery substance 1704. For example, the delivery substance 1704 may be a medical substance or drug that must be kept within a certain temperature range. The delivery substance 1704 may alternatively be a sensitive electrical or other component which must be electrically and/or thermally shielded.

Figure 23:
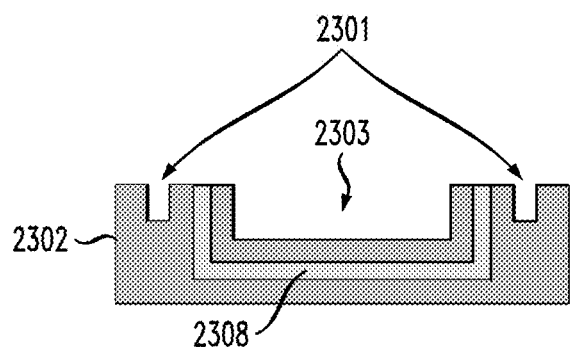
FIG. 23 depicts a side cross-sectional view of a bottom substrate having trenches and a thermal insulator layer formed therein, according to an embodiment of the present invention.

FIG. 23 shows a side cross-sectional view 2300 of a bottom substrate 2302, with trenches 2301 and a reservoir 2303 formed therein, similar in size and composition to the bottom substrate 1702, trenches 1701 and reservoir 1703, respectively. The bottom substrate 2302, however, also includes an additional layer 2308 that surrounds the reservoir 2303. The additional layer 2308 may be formed by dispensing paste followed by a curing process.

In some embodiments, the additional layer 2308 is a thermal insulator. The thermal insulator may be formed from rubber, epoxy, a rubber/epoxy mixed with $SiO_2$ particles, etc. The thermal insulator may have a thickness of 1-5 microns. The thickness of the thermal insulator may vary depending on the material or materials used for the bottom substrate 2302 and/or top substrate 2502. For example, Si has a higher thermal conductivity relative to glass, and thus a thicker thermal insulator may be used when the bottom substrate 2302 and/or top substrate 2502 is formed of Si.

In other embodiments, the additional layer 2308 is an electromagnetic shielding layer. The electromagnetic shielding layer may be, by way of example a polymer-carbon composite or other suitable material. The thickness of the electromagnetic shielding layer may by 1-5 microns. Similar to the thermal insulator layer described above, the electromagnetic shielding layer may have a thickness which varies based on electromagnetic properties of the materials used for the bottom substrate 2302 and/or top substrate 2502. It is also to be appreciated that in some embodiments the additional layer may include both a thermal insulator layer and an electromagnetic shielding layer.

Figure 24:
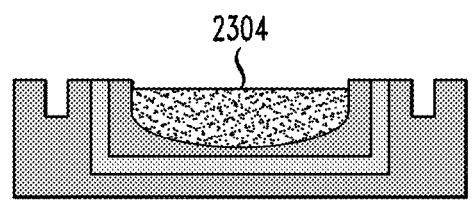
FIG. 24 depicts a side cross-sectional view of the FIG. 23 bottom substrate following formation of a delivery substance in one of the trenches, according to an embodiment of the present invention.

FIG. 24 shows a side cross-sectional view 2400 of the bottom substrate 2302 after delivery substance 2304 is placed in the reservoir 2303. The delivery substance 2304, similar to the delivery substance 1704, may be a medical substance or drug, a biosensor, a smart tag, an IoT device, some other type of electrical device, etc.

Figure 25:
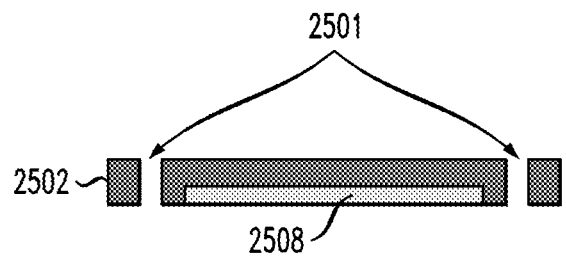
FIG. 25 depicts a side cross-sectional view of a top substrate having vias and a thermal insulator layer formed therein, according to an embodiment of the present invention.

FIG. 25 shows a side cross-sectional view 2500 of a top substrate 2502 having vias 2501 formed therein, similar in size and composition to the top substrate 1902 and vias 1901, respectively. The top substrate 2502 also has an additional layer 2508 formed therein. The additional layer 2508, similar to the additional layer 2308, may be a thermal insulator, an electrical shielding layer, etc. The materials and sizing of the additional layer 2508 may match that of the additional layer 2308.

Figure 26:
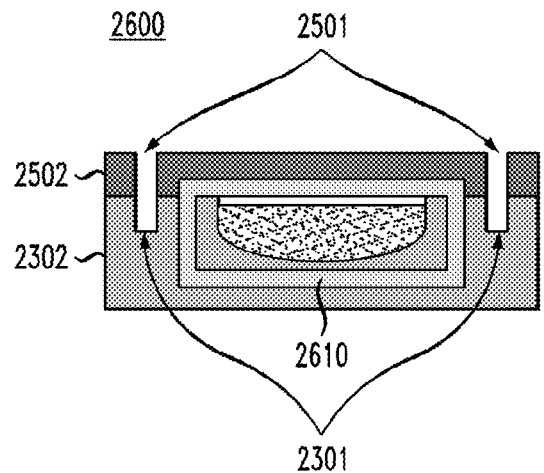
FIG. 26 depicts a side cross-sectional view of the top substrate of FIG. 25 aligned with the bottom substrate of FIG. 25, according to an embodiment of the present invention.

FIG. 26 shows a side cross-sectional view 2600 of the top substrate 2502 aligned with the bottom substrate 2302 such that the vias 2501 formed in the top substrate 2502 line up with the trenches 2301 formed in the bottom substrate 2302. Also, the additional layer 2508 in top substrate 2502 lines up with the additional layer 2308 in bottom substrate 2302 such that the additional layers 2508 and 2308 surround the cavity formed by the reservoir 2303 forming a continuous additional later 2610.

Figure 27:
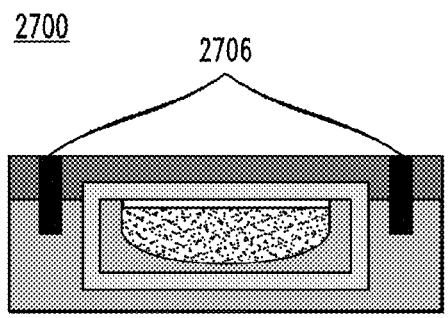
FIG. 27 depicts a side cross-sectional view of the aligned FIG. 26 structure following filling the vias and trenches to seal the top substrate of FIG. 25 to the bottom substrate of FIG. 24, according to an embodiment of the present invention.

FIG. 27 shows a side cross-sectional view 2700 of the aligned FIG. 26 structure wherein the top substrate 2502 and the bottom substrate 2302 are sealed together via solder fill material 2706.

Although not explicitly shown in FIG. 23-27, the trenches 2301 in bottom substrate 2302 and the vias 2501 in top substrate 2502 need not be the same size. For example, the vias 2501 in top substrate 2502 may be larger than the trenches 2301 in bottom substrate 2302, or vice versa. Also, while FIGS. 23-27 show that the trenches 2301 in bottom substrate 2302 and the vias 2501 in top substrate are uniform in size, embodiments are not so limited. One or both of the top substrate 2502 and the bottom substrate 2302 may have vias and/or trenches formed therein of different sizes.

Also, while not explicitly shown in FIGS. 23-27, liners similar to the liner 104 may be formed on sidewalls of one or more of the vias 2501 of top substrate 2502 and/or on sidewalls of one or more of the trenches 2301 of the bottom substrate 2302. Thus, the techniques described above with respect to FIGS. 1-7, including forming liners having solder adhesion layers, barrier layers, metal layers for formation of IMCs, etc. may be used for the vias 2301 in the top substrate 2302 and/or for the trenches 2501 of the bottom substrate 2502.

Similarly, the techniques shown and described with respect to FIGS. 17-27 may be used with other embodiments described herein. For example, the techniques for sealing a delivery substance may be used in heterogeneous layer stacking as described with respect to FIGS. 14-16. The use of IMS-filled vias for forming interconnects, as described in conjunction with FIGS. 1-16, may also be used in the context of FIGS. 17-27 to provide interconnects between the sealed structures and other layers or components of a larger structure, or within other embedded components of the sealed structures shown in FIG. 21, 22 or 27. By way of example, embedded passives such as embedded passives 1424-1, 1424-2 and 1424-3 may be embedded in the sealed structures of FIGS. 21, 22 and 27 so as to provide current or electric charge used to blow the seal for delivery of the delivery substance. The delivery may be triggered based on readings from biosensors (e.g., 1434) or silicon or other devise (e.g., 1416) embedded in the structures of FIGS. 21, 22 and 27.

Figure 28:
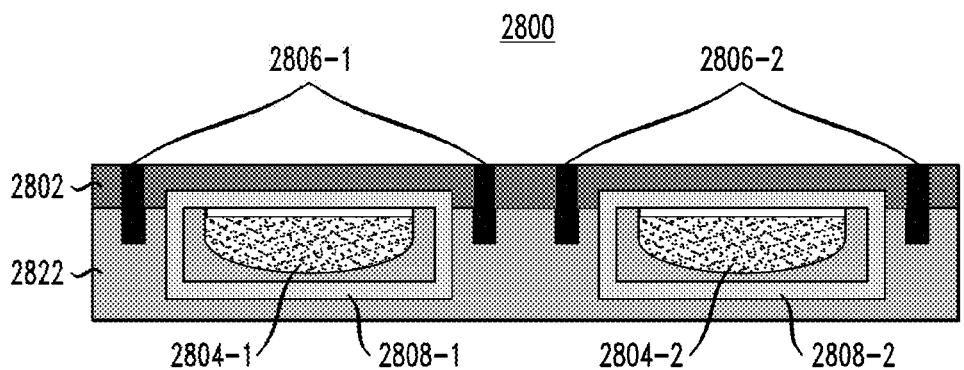
FIG. 28 depicts a side cross-sectional view of a top and bottom substrate sealing multiple different cavities, according to an embodiment of the present invention.

In some embodiments, multiple delivery substances are sealed into the same structure. For example, some types of medical treatments may require precise timing of medication delivery, such as combinations of different medical substances in precise times relative to one another, or for time-delayed delivery of a single type of medical substance. As will be appreciated, multiple reservoirs may be formed in a bottom substrate such as 1702 or 2302 to facilitate such use case scenarios. Multiple different seals may be used through the use of multiple sets of trenches and vias formed in bottom and top substrates. Different sets of additional layers may be used to isolate different reservoirs from one another. FIG. 28 shows an example of a structure with two reservoirs, but three or more reservoirs may be used in other embodiments.

As shown in FIG. 28, two delivery substances 2804-1 and 2804-2 are shown in cavities sealed between top substrate 2802 and bottom substrate 2822. Additional layer 2808-1 surrounds the cavity containing delivery substance 2804-1, and additional layer 2808-2 surrounds the cavity containing delivery substances 2804-2. The top substrate 2802 and bottom substrate 2822 are sealed via solder fill material 2806-1 and 2806-2 that fills vias formed in the top substrate 2802 and trenches formed in the bottom substrate 2822. Current may be selectively applied to solder fill materials 2806-1 and 2806-2 to control delivery of delivery substances 2804-1 and 2804-2 at different times or in response to different trigger conditions. In some embodiments, different solder fill materials may be used for 2806-1 and 2806-2, so as to facilitate such selective control. In other embodiments, the same material may be used and the delivery substances 2804-1 and 2804-2 may be delivered at the same or different times. In some cases, a medical substance or drug may have component parts that should only be mixed together at a particular predetermined time before use. Thus, such different portions may be isolated in the different cavities shown in FIG. 28 and then released and combined at the same time.

In some embodiments, using techniques described above with respect to FIGS. 17-28, a method includes forming one or more trenches in a first substrate, forming one or more vias in a second substrate, aligning at least a first trench in the first substrate with at least a first via in the second substrate and sealing the first substrate to the second substrate by filling the first via and the first trench with solder material using injection molded soldering. The method may further include depositing a delivery substance in a reservoir formed in the second substrate, wherein bonding the first substrate to the second substrate seals the delivery substance between the first substrate and the second substrate. This seal may be a hermetic seal. The delivery substance may be, by way of example, a medical substance, a biological sensor, an electronic device, etc.

The first trench may surround the reservoir to facilitate sealing the delivery substance. In some embodiments, the method also includes forming a first thermal insulator layer between the first trench and the reservoir and forming a second thermal insulator layer in the second substrate. In such cases, aligning the first trench in the first substrate with the first via in the second substrate further includes aligning the first thermal insulator layer and the second thermal insulator layer, and bonding the first substrate to the second substrate further includes connecting the first thermal insulator layer and the second thermal insulator layer to form a third thermal insulator layer surrounding a cavity comprising the reservoir.

The first substrate may comprise a first material and the second substrate may comprise a second material different than the first material. For example, the first material comprises one of silicon and glass. The filled first trench and first via may form an interconnect between the first substrate and the second substrate. In some cases, the first trench and first via are a same size and shape. In other embodiments, the first trench may have a first thickness and the first via may have a second thickness different than the first thickness.

In some embodiments, techniques described above with respect to FIGS. 1-7 may be used to form at least one liner on at least one sidewall of at least one of the first trench and the first via. As an example the liner may comprise a barrier layer, a solder adhesion layer, etc.

An apparatus may be formed using the above-described method, with such apparatus comprising a first substrate having one or more trenches formed therein and a second substrate having one or more vias formed therein. At least a first trench in the first substrate is aligned with at least a first via in the second substrate, and the first substrate is sealed to the second substrate via solder material filling the first trench and the first via, the solder material being filled using injection molded soldering. The apparatus may further include a sealed cavity between the first substrate and the second substrate, wherein the sealed cavity comprise a reservoir formed in the first substrate, the reservoir being surrounded by the first trench. The apparatus may also include a thermal insulator layer surrounding the sealed cavity, the thermal insulator layer comprising a first portion formed between the first trench and the reservoir in the first substrate and a second portion formed in the second substrate.

The above-described method may also be used to form a substance delivery device, with the substance delivery device comprising a first substrate having one or more trenches, a reservoir and a first thermal insulator layer formed therein, at least a first one of the trenches surrounding the reservoir, the first thermal insulator layer being formed between the first trench and the reservoir, a second substrate having one or more vias and a second thermal insulator layer formed therein, a sealed cavity between the first substrate and the second substrate, the sealed cavity comprising the reservoir, and a thermal insulator surrounding the sealed cavity, the thermal insulator comprising the first thermal insulator layer and the second thermal insulator layer. The first trench in the first substrate is aligned with at least a first via in the second substrate, and the first substrate is sealed to the second substrate via solder material filling the first trench and the first via, the solder material being filled using injection molded soldering. Various delivery substances, such as a medical substance, may be in the sealed cavity.

Various structures described above may be implemented in integrated circuits. The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. An apparatus comprising:
  a substrate having one or more vias formed therein;
  one or more interconnects disposed through respective ones of the one or more vias;
  wherein at least one of the interconnects extends from a top surface of the substrate through at least one of the vias to a bottom surface of the substrate, said at least one interconnect comprising:
    a first portion disposed on the top surface of the substrate surrounding said at least one via;
    a second portion disposed on the bottom surface of the substrate surrounding said at least one via; and
    a third portion connecting the first portion and the second portion;
  wherein the first portion, the second portion and the third portion of the at least one interconnect comprises injection molded solder material;
  a first photoresist layer disposed over a first region on the top surface of the substrate, wherein the first portion of the interconnect is disposed over a second region on the top surface of the substrate exposed by the first photoresist layer;
  an additional substrate;
  an oxide layer disposed on a top surface of the additional substrate; and
  a second photoresist layer having a first surface disposed over a third region on the bottom surface of the substrate and a second surface disposed on a top surface of the oxide layer, wherein the second portion of the interconnect is disposed over a fourth region on the bottom surface of the substrate exposed by the second photoresist layer.

2. The apparatus of claim 1, wherein the substrate comprises a glass substrate.

3. The apparatus of claim 1, wherein the substrate comprises a silicon substrate.

4. The apparatus of claim 1, wherein at least one of the vias has an aspect ratio of 25:1 or greater.

5. The apparatus of claim 1, wherein the first portion of the at least one interconnect disposed on the top surface of the substrate and the second portion of the at least one interconnect disposed on the bottom surface of the substrate are at least one of different sizes, different shapes and not aligned with one another.

6. The apparatus of claim 1, wherein the at least one interconnect further comprises:
   a fourth portion disposed on the top surface of the substrate distinct from the first portion of the at least one interconnect; and
   a fifth portion connecting the fourth portion and the second portion.

7. The apparatus of claim 6, wherein the first portion of the at least one interconnect and the fourth portion of the at least one interconnect are at least one of different sizes and different shapes.

8. The apparatus of claim 1, wherein the one or more vias in the substrate comprise a first via having a first thickness and at least a second via having a second thickness different than the first thickness.

9. The apparatus of claim 1, further comprising at least one liner disposed on at least one sidewall of at least one of the vias.

10. The apparatus of claim 9, wherein the substrate comprises a glass substrate and said at least one liner comprises a solder adhesion layer.

11. The apparatus of claim 9, wherein the substrate comprise a silicon substrate and said at least one liner comprises a barrier layer and a solder adhesion layer formed over the barrier layer.

12. The apparatus of claim 1, wherein the substrate comprises a first material and the additional substrate comprises a second material different than the first material.

13. The apparatus of claim 12, wherein the second material comprises one of a polyimide film and a silicon wafer.

14. An integrated circuit comprising:
   a glass interposer comprising a substrate having one or more vias formed therein; and
   one or more interconnects disposed through respective ones of the one or more vias;
   wherein at least one of the interconnects extends from a top surface of the substrate through at least one of the vias to a bottom surface of the substrate, said at least one interconnect comprising:
      a first portion disposed on the top surface of the substrate surrounding said at least one via;
      a second portion disposed on the bottom surface of the substrate surrounding said at least one via; and
      a third portion connecting the first portion and the second portion;
   wherein the first portion, the second portion and the third portion of the at least one interconnect comprises injection molded solder material;
   a first photoresist layer disposed over a first region on the top surface of the substrate, wherein the first portion of the interconnect is disposed over a second region on the top surface of the substrate exposed by the first photoresist layer;
   an additional substrate;
   an oxide layer disposed on a top surface of the additional substrate; and
   a second photoresist layer having a first surface disposed over a third region on the bottom surface of the substrate and a second surface disposed on a top surface of the oxide layer, wherein the second portion of the interconnect is disposed over a fourth region on the bottom surface of the substrate exposed by the second photoresist layer.

15. The integrated circuit of claim 14, wherein the first portion of the at least one interconnect disposed on the top surface of the substrate and the second portion of the at least one interconnect disposed on the bottom surface of the substrate are at least one of different sizes, different shapes and not aligned with one another.

16. The integrated circuit of claim 14, wherein the at least one interconnect further comprises:
   a fourth portion disposed on the top surface of the substrate distinct from the first portion of the interconnect; and
   a fifth portion connecting the fourth portion and the second portion;
   wherein the first portion of the at least one interconnect and the fourth portion of the at least one interconnect are at least one of different sizes and different shapes.

17. The integrated circuit of claim 14, the substrate comprises a first material and the additional substrate comprises a second material different than the first material.

18. The integrated circuit of claim 17, wherein the second material comprises one of a polyimide film and a silicon wafer.

19. The integrated circuit of claim 14, further comprising at least one liner disposed on at least one sidewall of at least one of the vias.

20. The integrated circuit of claim 19, wherein said at least one liner comprises a solder adhesion layer.

* * * * *